(12) United States Patent
Djupesland et al.

(10) Patent No.: US 8,171,929 B2
(45) Date of Patent: May 8, 2012

(54) DELIVERY DEVICE AND METHOD

(75) Inventors: Per Gisle Djupesland, Oslo (NO);
Keith McMurray Boden, Surrey (GB)

(73) Assignee: OptiNose AS, Oslo (NO)

(*) Notice: Subject to any disclaimer, the term of this patent is extended or adjusted under 35 U.S.C. 154(b) by 664 days.

(21) Appl. No.: 12/279,291

(22) PCT Filed: Feb. 14, 2007

(86) PCT No.: PCT/GB2007/000505
§ 371 (c)(1),
(2), (4) Date: May 14, 2009

(87) PCT Pub. No.: WO2007/093784
PCT Pub. Date: Aug. 23, 2007

(65) Prior Publication Data
US 2010/0051022 A1    Mar. 4, 2010

(30) Foreign Application Priority Data

Feb. 14, 2006  (GB) .................................. 0602980.5
Jul. 13, 2006  (GB) .................................. 0613934.9

(51) Int. Cl.
*A61M 11/00*  (2006.01)
*A61M 15/00*  (2006.01)

(52) U.S. Cl. .......... 128/200.23; 128/203.15; 128/203.18

(58) Field of Classification Search ............. 128/200.13, 128/200.14, 200.21, 200.22, 200.23, 203.12, 128/203.13, 203.15, 203.16, 203.18, 203.22, 128/203.23, 203.24, 203.26, 203.27

See application file for complete search history.

(56) References Cited

U.S. PATENT DOCUMENTS

| | | | | |
|---|---|---|---|---|
| 1,567,286 A * | 12/1925 | Moore et al. | ................... | 138/143 |
| 1,816,984 A * | 8/1931 | Miller | .............. | 165/68 |
| 2,161,466 A * | 6/1939 | Henneberg | ................ | 250/396 R |
| 2,279,285 A * | 4/1942 | Worth | .......................... | 236/34.5 |
| 2,279,291 A * | 4/1942 | Cheney | ......................... | 585/742 |
| 2,281,894 A * | 5/1942 | Von Fuchs et al. | ............. | 208/19 |
| 2,293,972 A * | 8/1942 | Dunn | .............................. | 164/53 |
| 2,303,667 A * | 12/1942 | Taborski | ......................... | 401/47 |

(Continued)

FOREIGN PATENT DOCUMENTS

WO    WO 2004/103447    12/2004

(Continued)

OTHER PUBLICATIONS

U.S. Appl. No. 11/567,286, filed Dec. 6, 2006, Djupesland.

(Continued)

*Primary Examiner* — Stephen Crow
(74) *Attorney, Agent, or Firm* — Proskauer Rose LLP

(57) ABSTRACT

A delivery device for and method of delivering substance to a nasal airway of a subject, the delivery device comprising: at least one nosepiece unit (21) for insertion into one nasal cavity of a subject and comprising a nosepiece (25) for fitting to the respective nostril of the subject; and at least one delivery unit (23) which is operative to deliver a substance through the at least one nosepiece unit into the one nasal cavity of the subject, wherein the at least one delivery unit includes a substance supply unit (27) for delivering a substance and an actuation unit (29) which is operable to actuate the substance supply unit, either automatically or manually, in response to nasal exhalation or at least attempted nasal exhalation by the subject.

37 Claims, 10 Drawing Sheets

U.S. PATENT DOCUMENTS

| | | | | |
|---|---|---|---|---|
| 2,339,716 A * | 1/1944 | Nachemov | | 33/25.3 |
| 2,375,115 A * | 5/1945 | Kylin | | 279/146 |
| 2,398,292 A * | 4/1946 | Delano | | 202/234 |
| 3,605,738 A | 9/1971 | Ciranna | | |
| 5,049,493 A * | 9/1991 | Khosla et al. | | 435/69.1 |
| 5,060,643 A * | 10/1991 | Rich et al. | | 128/200.23 |
| 5,069,204 A * | 12/1991 | Smith et al. | | 128/200.23 |
| 5,349,945 A * | 9/1994 | Wass et al. | | 128/200.23 |
| 5,355,873 A * | 10/1994 | Del Bon et al. | | 128/200.23 |
| 5,373,841 A * | 12/1994 | Kyllonen et al. | | 128/203.18 |
| 6,470,882 B1 * | 10/2002 | Newhouse et al. | | 128/200.24 |
| 6,715,485 B1 * | 4/2004 | Djupesland | | 128/203.15 |
| 6,948,495 B2 * | 9/2005 | Seppala | | 128/203.15 |
| 7,347,201 B2 * | 3/2008 | Djupesland | | 128/200.23 |
| 7,377,901 B2 * | 5/2008 | Djupesland et al. | | 600/529 |
| 7,481,218 B2 * | 1/2009 | Djupesland | | 128/206.11 |
| 7,740,014 B2 * | 6/2010 | Djupesland | | 128/207.18 |
| 7,784,460 B2 * | 8/2010 | Djupesland et al. | | 128/203.18 |
| 7,841,337 B2 * | 11/2010 | Djupesland | | 128/200.23 |
| 7,854,227 B2 * | 12/2010 | Djupesland | | 128/203.18 |
| 2004/0112378 A1 * | 6/2004 | Djupesland | | 128/203.12 |
| 2004/0112379 A1 * | 6/2004 | Djupesland | | 128/203.12 |
| 2004/0149289 A1 * | 8/2004 | Djupesland | | 128/207.18 |
| 2004/0182388 A1 * | 9/2004 | Djupesland | | 128/203.15 |
| 2005/0028812 A1 | 2/2005 | Djupesland | | |
| 2005/0056276 A1 | 3/2005 | Schuler et al. | | |
| 2005/0072430 A1 * | 4/2005 | Djupesland | | 128/206.11 |
| 2005/0235992 A1 * | 10/2005 | Djupesland | | 128/204.18 |
| 2005/0289629 A1 * | 12/2005 | Nadarajah | | 725/115 |
| 2006/0096589 A1 * | 5/2006 | Djupesland | | 128/200.14 |
| 2006/0169278 A1 * | 8/2006 | Djupesland et al. | | 128/200.14 |
| 2006/0219240 A1 * | 10/2006 | Djupesland | | 128/200.18 |
| 2006/0219241 A1 * | 10/2006 | Djupesland | | 128/200.18 |
| 2006/0225732 A1 * | 10/2006 | Djupesland | | 128/200.18 |
| 2006/0231094 A1 * | 10/2006 | Djupesland | | 128/203.15 |
| 2007/0039614 A1 * | 2/2007 | Djupesland | | 128/200.23 |
| 2007/0125371 A1 * | 6/2007 | Djupesland | | 128/200.14 |
| 2007/0186927 A1 * | 8/2007 | Djupesland et al. | | 128/203.15 |
| 2008/0161771 A1 * | 7/2008 | Djupesland | | 604/503 |
| 2008/0163874 A1 * | 7/2008 | Djupesland | | 128/207.18 |
| 2008/0221471 A1 * | 9/2008 | Djupesland et al. | | 600/543 |
| 2008/0223363 A1 * | 9/2008 | Djupesland | | 128/200.23 |
| 2008/0289629 A1 | 11/2008 | Djupesland | | |

FOREIGN PATENT DOCUMENTS

WO    WO 2005/075012    8/2005

OTHER PUBLICATIONS

U.S. Appl. No. 11/816,984, filed Aug. 23, 2007, Djupesland.
U.S. Appl. No. 12/161,466, filed Jul. 18, 2008, Djupesland.
U.S. Appl. No. 12/279,285, filed Aug. 13, 2008, Djupesland.
U.S. Appl. No. 12/281,547, filed Sep. 3, 2008, Djupesland.
U.S. Appl. No. 12/281,894, filed Sep. 5, 2008, Djupesland.
U.S. Appl. No. 12/293,972, filed Sep. 22, 2008, Djupesland.
U.S. Appl. No. 12/298,292, filed Oct. 23, 2008, Djupesland.
U.S. Appl. No. 12/303,667, filed Dec. 5, 2008, Djupesland.
U.S. Appl. No. 12/339,716, filed Dec. 19, 2008, Djupesland.
U.S. Appl. No. 12/375,115, filed Jan. 26, 2009, Djupesland.
International Search Report for International Application No. PCT/GB2007/000505, Date of Mailing May 11, 2007 (3 pages).

* cited by examiner

DELIVERY DEVICE AND METHOD

The present invention relates to a delivery device for and a method of delivering a substance, in particular one of a liquid, as a suspension or solution, or a powder containing a medicament, especially systemic or topical pharmaceuticals, or a vaccine to the nasal airway of a subject.

Referring to FIG. 13, the nasal airway 1 comprises the two nasal cavities separated by the nasal septum, which airway 1 includes numerous ostia, such as the paranasal sinus ostia 3 and the tubal ostia 5, and olfactory cells, and is lined by the nasal mucosa. The nasal airway 1 can communicate with the nasopharynx 7, the oral cavity 9 and the lower airway 11, with the nasal airway 1 being in selective communication with the anterior region of the nasopharynx 7 and the oral cavity 9 by opening and closing of the oropharyngeal velum 13. The velum 13, which is often referred to as the soft palate, is illustrated in solid line in the closed position, as achieved by providing a certain positive pressure in the oral cavity 9, such as achieved on exhalation through the oral cavity 9, and in dashed line in the open position.

There are many nasal conditions which require treatment. One such condition is nasal inflammation, specifically rhinitis, which can be allergic or non-allergic and is often associated with infection and prevents normal nasal function. By way of example, allergic and non-allergic inflammation of the nasal airway can typically effect between 10 and 20% of the population, with nasal congestion of the erectile tissues of the nasal concha, lacrimation, secretion of watery mucus, sneezing and itching being the most common symptoms. As will be understood, nasal congestion impedes nasal breathing and promotes oral breathing, leading to snoring and sleep disturbance. Other nasal conditions include nasal polyps which arise from the paranasal sinuses, hypertrophic adenoids, secretory otitis media, sinus disease and reduced olfaction.

In the treatment of certain nasal conditions, the topical administration of medicaments is preferable, particularly where the nasal mucosa is the prime pathological pathway, such as in treating or relieving nasal congestion. Medicaments that are commonly topically delivered include decongestants, anti-histamines, cromoglycates, steroids and antibiotics. At present, among the known anti-inflammatory pharmaceuticals, topical steroids have been shown to have an effect on nasal congestion. Topical decongestants have also been suggested for use in relieving nasal congestion. The treatment of hypertrophic adenoids and chronic secretory otitis media using topical decongestants, steroids and anti-microbial agents, although somewhat controversial, has also been proposed. Further, the topical administration of pharmaceuticals has been used to treat or at least relieve symptoms of inflammation in the anterior region of the nasopharynx, the paranasal sinuses and the auditory tubes.

Medicaments can also be systemically delivered through the nasal pathway, the nasal pathway offering a good administration route for the systemic delivery of pharmaceuticals, such as hormones, for example, oxytocin and calcitonin, and analgetics, such as anti-migraine compositions, as the high blood flow and large surface area of the nasal mucosa advantageously provides for rapid systemic uptake.

Nasal delivery is also expected to be advantageous for the administration of medicaments requiring a rapid onset of action, for example, analgetics, anti-emetics, insulin, anti-epileptics, sedatives and hypnotica, and also other pharmaceuticals, for example, cardio-vascular drugs. It is envisaged that nasal administration will provide for a fast onset of action, at a rate similar to that of injection and at a rate much faster than that of oral administration. Indeed, for the treatment of many acute conditions, nasal administration is advantageous over oral administration, since gastric stasis can further slow the onset of action following oral administration.

It is also expected that nasal delivery could provide an effective delivery route for the administration of proteins and peptides as produced by modern biotechnological techniques. For such substances, the metabolism in the intestines and the first-pass-effect in the liver represent significant obstacles for reliable and cost-efficient delivery.

Furthermore, it is expected that nasal delivery using the nasal delivery technique of the present invention will prove effective in the treatment of many common neurological diseases, such as Alzheimer's, Parkinson's, psychiatric diseases and intracerebral infections, where not possible using existing techniques. The nasal delivery technique of the present invention allows for delivery to the olfactory region, which region is located in the superior region of the nasal cavities and represents the only region where it is possible to circumvent the blood-to-brain barrier (BBB) and enable communication with the cerebrospinal fluid (CSF) and the brain.

Also, it is expected that the nasal delivery technique of the present invention will allow for the effective delivery of vaccines.

Aside from the delivery of medicaments, the irrigation of the nasal mucosa with liquids, in particular saline solutions, is commonly practised to remove particles and secretions, as well as to improve the mucociliary activity of the nasal mucosa. These solutions can be used in combination with active pharmaceuticals.

For any kind of drug delivery, accurate and reliable dosing is essential, but it is of particular importance in relation to the administration of potent drugs which have a narrow therapeutic window, drugs with potentially serious adverse effects and drugs for the treatment of serious and life-threatening conditions. For some conditions, it is essential to individualize the dosage to the particular situation, for example, in the case of diabetes mellitus. For diabetes, and, indeed, for many other conditions, the dosage of the pharmaceutical is preferably based on actual real-time measurements.

Currently, blood samples are most frequently used, but the analysis of molecules in the exhalation breath of subjects has been proposed as an alternative to blood analysis for several conditions. Breath analysis is currently used for the diagnosis of conditions such as *helicobacter pylori* infections which cause gastric ulcers.

WO-A-00/51672 discloses a delivery device for delivering a substance, in particular a medicament, in a bi-directional flow through the nasal cavities, that is, an air flow which passes into one nostril, around the posterior margin of the nasal septum and in the opposite direction out of the other nostril. This bi-directional air flow advantageously acts to stimulate the sensory nerves in the nasal mucosa, thereby conditioning the subject for the delivery and providing a more comfortable delivery situation.

It is an aim of the present invention to provide an alternative delivery device and method for providing for delivery of substance to a nasal airway of subject.

In one aspect the present invention provides a delivery device and method which provides for delivery of a substance to a nasal airway of a subject in response to exhalation or at least attempted exhalation through the nasal airway.

In one preferred aspect the present invention provides a delivery device for delivering substance to a nasal airway of a subject, the delivery device comprising: at least one nosepiece unit for insertion into one nasal cavity of a subject and comprising a nosepiece for fitting to the respective nostril of the subject; and at least one delivery unit which is operative to deliver a substance through the at least one nosepiece unit into the one nasal cavity of the subject, wherein the at least one delivery unit includes a substance supply unit for delivering a substance and an actuation unit which is operable to actuate the substance supply unit in response to nasal exhalation or at least attempted nasal exhalation by the subject.

In one embodiment the substance supply unit is configured to deliver an aerosol spray.

In one embodiment the aerosol spray is a liquid aerosol.

In another embodiment the aerosol spray is a powder aerosol.

In another embodiment the substance supply unit is configured to deliver a liquid jet.

In a further embodiment the substance supply unit is configured to deliver a powder jet.

In one embodiment the nosepiece is configured to provide a fluid-tight seal with the one nostril of the subject.

In one embodiment the actuation unit includes a pressure sensor for sensing the pressure at the nosepiece and actuating the substance supply unit in response to a predeterminable pressure.

In another embodiment the actuation unit includes a flow sensor for sensing the flow rate at the nosepiece and actuating the substance supply unit in response to a predeterminable flow rate.

In a further embodiment the actuation unit includes a pressure sensor for sensing the pressure at the nosepiece and is operative such as to allow for manual actuation of the substance supply unit only in response to the pressure sensor sensing a predeterminable pressure.

In a still further embodiment the actuation unit includes a flow sensor for sensing the flow rate at the nosepiece and is operative such as to allow for manual actuation of the substance supply unit only in response to the flow sensor sensing a predeterminable flow rate.

In one embodiment the substance supply unit is configured to deliver substance with sufficient force as to be directed to a posterior region of the one nasal cavity, and be entrained by an exhalation air flow through the other nasal cavity.

In another embodiment the substance supply unit is configured to deliver substance into the one nasal cavity, and be drawn from the one nasal cavity by an exhalation air flow through the other nasal cavity.

In one embodiment the delivery device comprises: first and second nosepiece units for fitting to the respective nostrils of the subject, wherein the substance supply unit is in fluid communication with the first nosepiece unit such that substance is in use delivered into the one nasal cavity and the actuation unit is in fluid communication with the second, outlet nosepiece unit.

In one embodiment the delivery unit includes a filter unit which is in fluid communication with the second, outlet nosepiece unit.

In one embodiment the actuation unit includes a release mechanism which is manually operable to unlock the actuation unit, such as to render the actuation unit operative in response to nasal exhalation or at least attempted nasal exhalation by the subject.

In one embodiment the release mechanism comprises a movable member which is manually operable between a first, locking configuration in which the actuation unit is locked to prevent operation in response to nasal exhalation or at least attempted nasal exhalation by the subject, and a second, unlocked configuration in which the actuation unit is unlocked to allow for operation in response to nasal exhalation or at least attempted exhalation by the subject.

In one embodiment the movable member in use extends into the other nasal cavity, such that the other nostril of the subject is closed when the movable member is in the unlocked configuration.

In another preferred aspect the present invention provides a method of delivering substance to a nasal airway of a subject, the method comprising the steps of: providing a delivery device comprising a nosepiece unit including a nosepiece for fitting to one nasal cavity of a subject, and a delivery unit including a substance supply unit for delivering substance and an actuation unit which is operable to actuate the substance supply unit in response to nasal exhalation or at least attempted nasal exhalation by the subject; fitting the nosepiece unit to one nasal cavity of a subject; the subject exhaling nasally or at least attempting to exhale nasally; and actuating the substance supply unit to deliver substance to the one nasal cavity in response to nasal exhalation or at least attempted nasal exhalation.

In one embodiment the substance supply unit is delivered as an aerosol spray.

In one embodiment the aerosol spray is a liquid aerosol.

In another embodiment the aerosol spray is a powder aerosol.

In another embodiment the substance is delivered as a liquid jet.

In a further embodiment the substance is delivered as a powder jet.

In one embodiment the actuation unit includes a pressure sensor for sensing the pressure at the nosepiece and is operative to actuate the substance supply unit in response to the pressure sensor sensing a predeterminable pressure.

In another embodiment the actuation unit includes a flow sensor for sensing the flow rate at the nosepiece and is operative to actuate the substance supply unit in response to the flow sensor sensing a predeterminable flow rate.

In a further embodiment the actuation unit includes a pressure sensor for sensing the pressure at the nosepiece and is configured such as to allow for manual actuation of the substance supply unit only in response to the pressure sensor sensing a predeterminable pressure, and the actuating step comprises the step of: manually actuating the substance supply unit to deliver substance to the one nasal cavity.

In a still further embodiment the actuation unit includes a flow sensor for sensing the flow rate at the nosepiece and is configured such as to allow for manual actuation of the substance supply unit only in response to the flow sensor sensing a predeterminable flow rate, and the actuating step comprises the step of: manually actuating the substance supply unit to deliver substance to the one nasal cavity.

In one embodiment the nosepiece unit is configured to close the one nostril of the subject.

In another embodiment the nosepiece unit is configured to allow an air flow from the one nostril of the subject on nasal exhalation by the subject.

In one embodiment the substance supply unit is configured to deliver substance with sufficient force as to be directed to a posterior region of the one nasal cavity, and an exhalation air flow is generated through the other nasal cavity which acts to entrain the delivered substance.

In another embodiment the substance supply unit is configured to deliver substance into the one nasal cavity, and an exhalation air flow is generated through the other nasal cavity which acts to draw the delivered substance from the one nasal cavity.

In one embodiment the delivery device comprises first and second nosepiece units for fitting to the respective nostrils of the subject, wherein the substance supply unit is in fluid communication with the first nosepiece unit such that substance is delivered into the one nasal cavity and the actuation unit is in fluid communication with the second, outlet nosepiece unit.

In one embodiment the delivery unit includes a filter unit which is in fluid communication with the second, outlet nosepiece unit and acts to trap any substance as delivered from the other nostril of the subject.

In one embodiment the actuation unit includes a release mechanism which is manually operable to unlock the actuation unit, such as to render the actuation unit operative in response to nasal exhalation or at least attempted nasal exhalation by the subject.

In one embodiment the release mechanism comprises a movable member which is manually operable between a first, locking configuration in which the actuation unit is locked to prevent operation in response to nasal exhalation or at least attempted nasal exhalation by the subject, and a second, unlocked configuration in which the actuation unit is unlocked to allow for operation in response to nasal exhalation or at least attempted nasal exhalation by the subject.

In one embodiment the movable member extends into the other nasal cavity, such that movement of the movable member to the unlocked configuration requires closure of the other nostril of the subject.

Preferred embodiments of the present invention will now be described hereinbelow by way of example only with reference to the accompanying drawings, in which:

FIG. 1 illustrates a nasal delivery device in accordance with a first embodiment of the present invention;

FIGS. 2(a) to (c) illustrate one mode of operation of the nasal delivery device of FIG. 1;

FIGS. 3(a) to (c) illustrate another mode of operation of the nasal delivery device of FIG. 1;

FIG. 4 illustrates a nasal delivery device in accordance with a second embodiment of the present invention;

FIGS. 5(a) to (c) illustrate one mode of operation of the nasal delivery device of FIG. 4;

FIGS. 6(a) to (c) illustrate another mode of operation of the nasal delivery device of FIG. 4;

FIG. 7 illustrates a nasal delivery device in accordance with a third embodiment of the present invention;

FIGS. 8(a) to (c) illustrate one mode of operation of the nasal delivery device of FIG. 7;

FIGS. 9(a) to (c) illustrate another mode of operation of the nasal delivery device of FIG. 7;

FIG. 10 illustrates a nasal delivery device in accordance with a fourth embodiment of the present invention;

FIGS. 11(a) to (c) illustrate one mode of operation of the nasal delivery device of FIG. 10;

FIGS. 12(a) to (c) illustrate another mode of operation of the nasal delivery device of FIG. 10;

FIG. 13 schematically illustrates a nasal delivery device in accordance with a fifth embodiment of the present invention;

Figure 1:
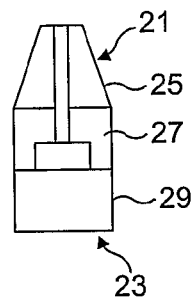
FIGS. 1 to 3 illustrate a nasal delivery device in accordance with a first embodiment of the present invention.

The delivery device comprises a nosepiece unit 21 for fitting to one nostril of a subject, and a delivery unit 23 for delivering substance through the nosepiece unit 21 into the nasal cavity in response to exhalation by the subject through the nasal airway.

The nosepiece unit 21 includes a nosepiece 25 through which substance is delivered into the nasal cavity of the subject.

In this embodiment the nosepiece 25 comprises a tubular, frusto-conical element which is configured such as to be inserted into one nostril, and in a preferred embodiment provide a fluid-tight seal with the one nostril.

In an alternative embodiment the nosepiece 25 could comprise an annular element which is configured such as to engage the nares of the one nostril, and in a preferred embodiment provide a fluid-tight seal with the one nostril.

The delivery unit 23 includes a substance supply unit 27 for delivering a dose of a substance, in this embodiment a metered dose of a substance, and an actuation unit 29, in this embodiment a breath-actuation unit, which is in fluid communication with the nosepiece 25 and is operative to actuate the substance supply unit 27 in response to exhalation by the subject through the nasal airway.

In this embodiment the substance supply unit 27 comprises a liquid supply unit for delivering a liquid substance through the nosepiece 25.

In another embodiment the substance supply unit 27 could comprise a powder supply unit for delivering a powdered substance through the nosepiece 25.

In this embodiment the substance supply unit 27 comprises an aerosol generator for delivering an aerosol of the substance through the nosepiece 25.

In an alternative embodiment the substance supply unit 27 could comprise a jet generator for delivering a jet of the substance through the nosepiece 25.

In this embodiment the substance comprises a medicament, but the substance could be any kind of other substance, such as a vaccine.

In this embodiment the substance supply unit 27 comprises a pump unit, here a mechanical pump unit.

In an alternative embodiment the substance supply unit 27 could comprise an electrically-operated pump unit.

In another embodiment the substance supply unit 27 could comprise a nebulizer for delivering an aerosol, either as a liquid or powder aerosol, to the nosepiece 25.

In this embodiment the actuation unit 29 includes a pressure sensor for sensing the pressure at the nosepiece 25 and actuating the substance supply unit 27 in response to generation of a predetermined pressure.

In another embodiment the actuation unit 29 could include a flow sensor for sensing a flow through the nosepiece 25 and actuating the substance supply unit 27 in response to detection of a predetermined flow.

One mode of operation of the above-described delivery device will now be described hereinbelow with reference to FIGS. 2(a) to (c) of the accompanying drawings.

Figure 2A:
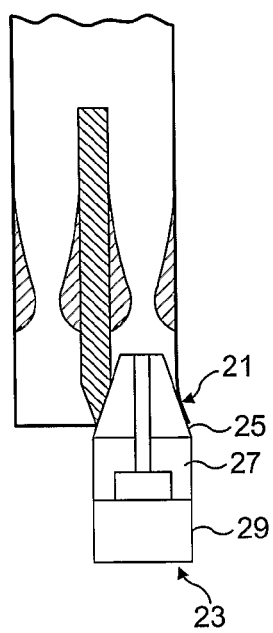

The subject first primes the delivery unit 21, in this embodiment by loading a biasing element, fits the nosepiece 25 to one nostril, as illustrated in FIG. 2(a), and the subject then exhales through his or her nasal airway.

Figure 2B:
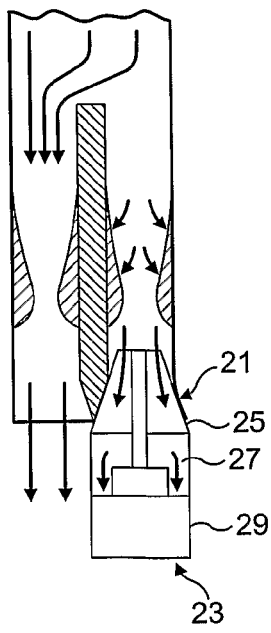
Figure 2C:
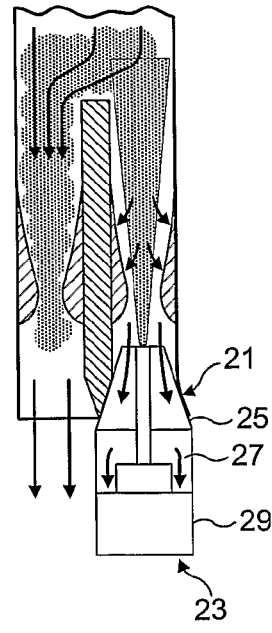

In this embodiment, where the one nasal cavity is closed, on exhaling through the nasal airway, a pressure is developed in the one nasal cavity to which the delivery device is fitted and an exhalation air flow is developed through the other nasal cavity, as illustrated in FIG. 2(b). As illustrated in FIG. 2(b), the pressure which is developed in the one nasal cavity acts to expand the nasal valve therein, thereby facilitating the delivery of substance to posterior regions of the nasal airway. On generation of a predetermined pressure at the nosepiece 25, the actuation unit 29 acts to actuate the substance supply unit 27 to deliver substance through the nosepiece 25 and into the one nasal cavity, as illustrated in FIG. 2(c).

In one embodiment the substance supply unit 27 is configured to deliver substance with sufficient force as to be directed to a posterior region of the one nasal cavity, and be entrained by the exhalation air flow through the other nasal cavity. In this way, substance is entrained around the nasal septum, providing for improved delivery to the posterior region of the nasal airway.

In an alternative embodiment the substance supply unit 27 could be configured to deliver substance into the nosepiece 25, which substance becomes resident in the one nasal cavity and is drawn, in the manner of the Venturi effect, into the exhalation air flow through the other nasal cavity. In this way, substance is delivered around the nasal septum, providing for improved delivery to the posterior region of the nasal airway.

In one embodiment, and where required, the delivery device can be utilized to deliver substance to the respective nasal cavities of the subject by repeating the delivery operation.

Another mode of operation of the above-described delivery device will now be described hereinbelow with reference to FIGS. 3(*a*) to (*c*) of the accompanying drawings.

Figure 3A:
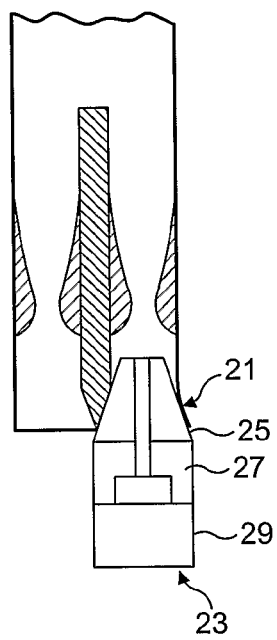
Figure 3B:
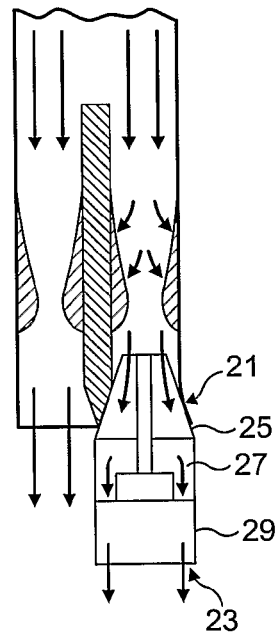
Figure 3C:
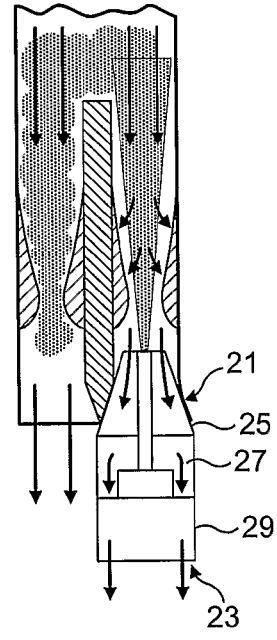

The subject first primes the delivery unit 21, in this embodiment by loading a biasing element, fits the nosepiece 25 to one nostril, as illustrated in FIG. 3(*a*), and the subject then exhales through his or her nasal airway.

In this embodiment, where the one nasal cavity is open to allow a flow therethrough, on exhaling through the nasal airway, a pressure is developed in the one nasal cavity to which the delivery device is fitted and an exhalation air flow is developed through the other nasal cavity, as illustrated in FIG. 3(*b*). As illustrated in FIG. 3(*b*), the pressure which is developed in the one nasal cavity acts to expand the nasal valve therein, thereby facilitating the delivery of substance to posterior regions of the nasal airway.

On generation of a predetermined flow at the nosepiece 25, the actuation unit 29 acts to actuate the substance supply unit 27 to deliver substance through the nosepiece 25 and into the one nasal cavity, as illustrated in FIG. 3(*c*).

In one embodiment the substance supply unit 27 is configured to deliver substance with sufficient force as to be directed to a posterior region of the one nasal cavity, and be entrained by the exhalation air flow through the other nasal cavity. In this way, substance is entrained around the nasal septum, providing for improved delivery to the posterior region of the nasal airway.

In an alternative embodiment the substance supply unit 27 could be configured to deliver substance into the nosepiece 25, which substance becomes resident in the one nasal cavity and is drawn, in the manner of the Venturi effect, into the exhalation air flow through the other nasal cavity. In this way, substance is delivered around the nasal septum, providing for improved delivery to the posterior region of the nasal airway.

In one embodiment, and where required, the delivery device can be utilized to deliver substance to the respective nasal cavities of the subject by repeating the delivery operation.

Figure 4:
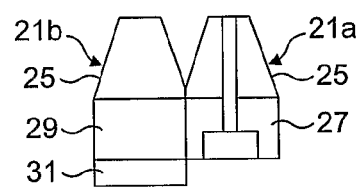
Figures 5A, 5B, 5C:
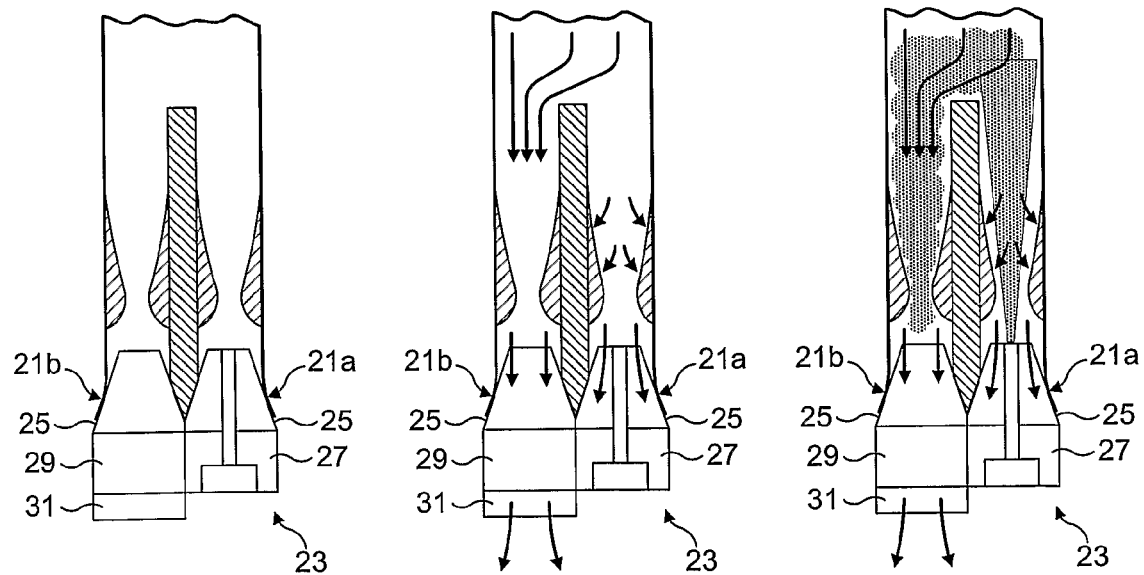
Figure 6A:
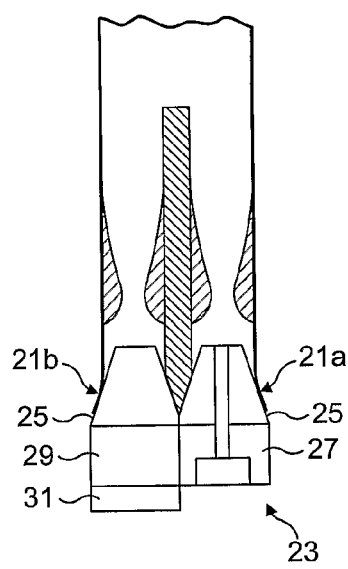
Figure 6B:
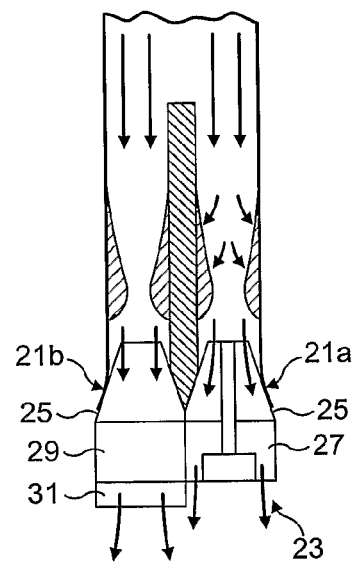

FIGS. 4 to 6 illustrate a nasal delivery device in accordance with a second embodiment of the present invention.

The delivery device of this embodiment is quite similar to the delivery device of the above-described first embodiment, and thus, in order to avoid unnecessary duplication of description of description, only the differences will be described in detail, with like parts being designated by like reference signs.

The delivery device of this embodiment differs from that of the above-described first embodiment in comprising first and second nosepiece units 21*a*, 21*b*, each including a nosepiece 25, for fitting to the respective nostrils of the subject, with the substance supply unit 27 being in fluid communication with the first, inlet nosepiece unit 21*a* such that substance is delivered into the one nasal cavity and the actuation unit 29 being in fluid communication with the second, outlet nosepiece unit 21*b*.

In this embodiment the delivery unit 23 also further comprises a filter unit 31 which is in fluid communication with the second, outlet nosepiece unit 21*b*, such as to trap any substance which would otherwise exit the other nostril.

One mode of operation of the above-described delivery device will now be described hereinbelow with reference to FIGS. 5(*a*) to (*c*) of the accompanying drawings.

The subject first primes the delivery unit 23, in this embodiment by loading a biasing element, fits the nosepieces 25 of the nosepiece units 21*a*, 21*b* to the respective nostrils, as illustrated in FIG. 5(*a*), and then exhales through his or her nasal airway.

In this embodiment, where the one nasal cavity is closed, on exhaling through the nasal airway, a pressure is developed in the one nasal cavity to which the delivery device is fitted and an exhalation air flow is developed through the other nasal cavity, as illustrated in FIG. 5(*b*). As illustrated in FIG. 5(*b*), the pressure which is developed in the one nasal cavity acts to expand the nasal valve therein, thereby facilitating the delivery of substance to posterior regions of the nasal airway. On generation of a predetermined flow through the other nasal cavity as detected by the actuation unit 29, the actuation unit 29 acts to actuate the substance supply unit 27 to deliver substance through the nosepiece 25 of the inlet nosepiece unit 21*a* and into the one nasal cavity, as illustrated in FIG. 5(*c*).

In one embodiment the substance supply unit 27 is configured to deliver substance with sufficient force as to be directed to a posterior region of the one nasal cavity, and be entrained by the exhalation air flow through the other nasal cavity. In this way, substance is entrained around the nasal septum, providing for improved delivery to the posterior region of the nasal airway.

In an alternative embodiment the substance supply unit 27 could be configured to deliver substance into the nosepiece 25 of the inlet nosepiece unit 21*a*, which substance becomes resident in the one nasal cavity and is drawn, in the manner of the Venturi effect, into the exhalation air flow through the other nasal cavity. In this way, substance is delivered around the nasal septum, providing for improved delivery to the posterior region of the nasal airway.

Another mode of operation of the above-described delivery device will now be described hereinbelow with reference to FIGS. 6(*a*) to (*c*) of the accompanying drawings.

The subject first primes the delivery unit 23, in this embodiment by loading a biasing element, fits the nosepieces 25 of the nosepiece units 21*a*, 21*b* to the respective nostrils, as illustrated in FIG. 6(*a*), and then exhales through his or her nasal airway.

Figure 6C:
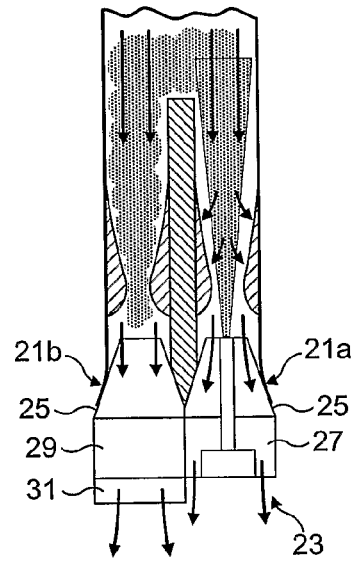

In this embodiment, where the one nasal cavity is open to allow a flow therethrough, on exhaling through the nasal airway, a pressure is developed in the one nasal cavity to which the delivery device is fitted and an exhalation air flow is developed through the other nasal cavity, as illustrated in FIG. 6(*b*). As illustrated in FIG. 6(*b*), the pressure which is developed in the one nasal cavity acts to expand the nasal valve therein, thereby facilitating the delivery of substance to posterior regions of the nasal airway. On generation of a predetermined flow through the other nasal cavity as detected by the actuation unit 29, the actuation unit 29 acts to actuate the substance supply unit 27 to deliver substance through the nosepiece 25 of the inlet nosepiece unit 21a and into the one nasal cavity, as illustrated in FIG. 6(c).

In one embodiment the substance supply unit 27 is configured to deliver substance with sufficient force as to be directed to a posterior region of the one nasal cavity, and be entrained by the exhalation air flow through the other nasal cavity. In this way, substance is entrained around the nasal septum, providing for improved delivery to the posterior region of the nasal airway.

In an alternative embodiment the substance supply unit 27 could be configured to deliver substance into the nosepiece 25 of the inlet nosepiece unit 21a, which substance becomes resident in the one nasal cavity and is drawn, in the manner of the Venturi effect, into the exhalation air flow through the other nasal cavity. In this way, substance is delivered around the nasal septum, providing for improved delivery to the posterior region of the nasal airway.

Figure 7:
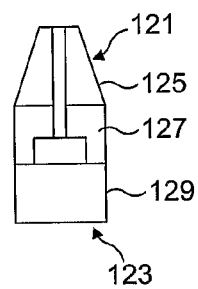

FIGS. 7 to 9 illustrate a nasal delivery device in accordance with a third embodiment of the present invention.

The delivery device comprises a nosepiece unit 121 for fitting to one nostril of a subject, and a delivery unit 123 which is operable to deliver substance through the nosepiece unit 121 into the nasal cavity of the subject.

The nosepiece unit 121 includes a nosepiece 125 through which substance is delivered into the nasal cavity of the subject.

In this embodiment the nosepiece 125 comprises a tubular, frusto-conical element which is configured such as to be inserted into one nostril, and in a preferred embodiment provide a fluid-tight seal with the one nostril.

In an alternative embodiment the nosepiece 125 could comprise an annular element which is configured such as to engage the nares of the one nostril, and in a preferred embodiment provide a fluid-tight seal with the one nostril.

The delivery unit 123 includes a substance supply unit 127 for delivering a dose of a substance, in this embodiment a metered dose of a substance, and an actuation unit 129, in this embodiment a manually-actuatable unit, which is in fluid communication with the nosepiece 125 and configured to allow for manual actuation of the substance supply unit 127 only in response to exhalation by the subject through the nasal airway.

In this embodiment the substance supply unit 127 comprises a liquid supply unit for delivering a liquid substance through the nosepiece 125.

In another embodiment the substance supply unit 127 could comprise a powder supply unit for delivering a powdered substance through the nosepiece 125.

In this embodiment the substance supply unit 127 comprises an aerosol generator for delivering an aerosol of the substance through the nosepiece 125.

In an alternative embodiment the substance supply unit 127 could comprise a jet generator for delivering a jet of the substance through the nosepiece 125.

In this embodiment the substance comprises a medicament, but the substance could be any kind of other substance, such as a vaccine.

In this embodiment the substance supply unit 127 comprises a pump unit, here a mechanical pump unit.

In an alternative embodiment the substance supply unit 127 could comprise an electrically-operated pump unit.

In another embodiment the substance supply unit 127 could comprise a nebulizer for delivering an aerosol, either as a liquid or powder aerosol, to the nosepiece 125.

In this embodiment the actuation unit 129 includes a pressure sensor for sensing the pressure at the nosepiece 125 and is configured to allow for manual actuation of the substance supply unit 127 only in response to generation of a predetermined pressure.

In another embodiment the actuation unit 129 could include a flow sensor for sensing a flow through the nosepiece 125 and be configured to allow for manual actuation of the substance supply unit 127 only in response to detection of a predetermined flow.

One mode of operation of the above-described delivery device will now be described hereinbelow with reference to FIGS. 8(a) to (c) of the accompanying drawings.

Figure 8A:
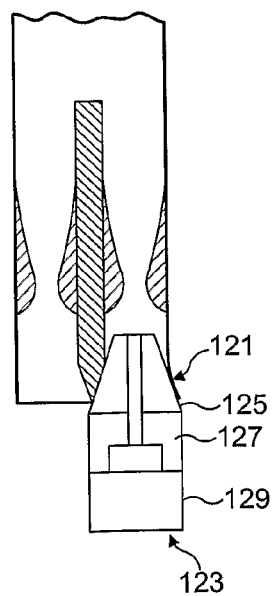

The subject first primes the delivery unit 121, in this embodiment by loading a biasing element, fits the nosepiece 125 to one nostril, as illustrated in FIG. 8(a), and the subject then exhales through his or her nasal airway.

Figure 8B:
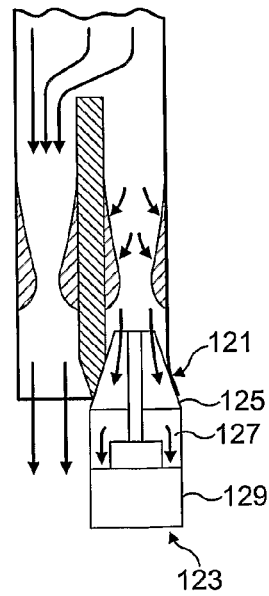

In this embodiment, where the one nasal cavity is closed, on exhaling through the nasal airway, a pressure is developed in the one nasal cavity to which the delivery device is fitted and an exhalation air flow is developed through the other nasal cavity, as illustrated in FIG. 8(b). As illustrated in FIG. 8(b), the pressure which is developed in the one nasal cavity acts to expand the nasal valve therein, thereby facilitating the delivery of substance to posterior regions of the nasal airway.

On generation of a predetermined pressure at the nosepiece 125, the actuation unit 129 is configured such as to be manually actuatable. In this embodiment the actuation unit 129 provides an indication to the user, typically as one or more of an audible, visual or tactile indication, when the predetermined pressure is generated at the nosepiece 125.

Figure 8C:
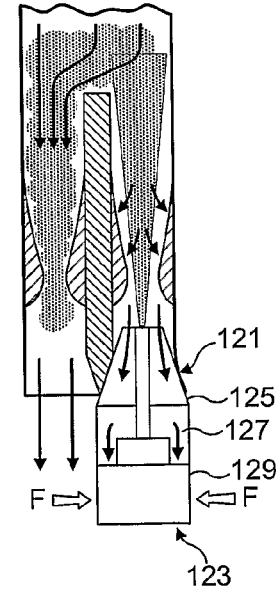

The user then actuates the substance supply unit 127 to deliver substance through the nosepiece 125 and into the one nasal cavity, as illustrated in FIG. 8(c).

In one embodiment the substance supply unit 127 is configured to deliver substance with sufficient force as to be directed to a posterior region of the one nasal cavity, and be entrained by the exhalation air flow through the other nasal cavity. In this way, substance is entrained around the nasal septum, providing for improved delivery to the posterior region of the nasal airway.

In an alternative embodiment the substance supply unit 127 could be configured to deliver substance into the nosepiece 125, which substance becomes resident in the one nasal cavity and is drawn, in the manner of the Venturi effect, into the exhalation air flow through the other nasal cavity. In this way, substance is delivered around the nasal septum, providing for improved delivery to the posterior region of the nasal airway.

In one embodiment, and where required, the delivery device can be utilized to deliver substance to the respective nasal cavities of the subject by repeating the delivery operation.

Another mode of operation of the above-described delivery device will now be described hereinbelow with reference to FIGS. 9(a) to (c) of the accompanying drawings.

Figure 9A:
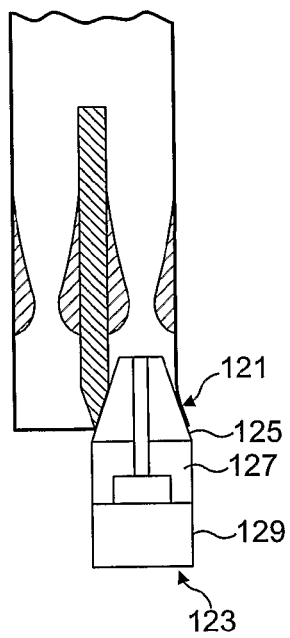

The subject first primes the delivery unit 121, in this embodiment by loading a biasing element, fits the nosepiece 125 to one nostril, as illustrated in FIG. 9(a), and the subject then exhales through his or her nasal airway.

Figure 9B:
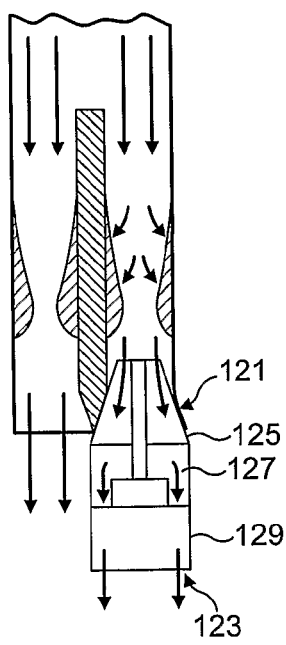

In this embodiment, where the one nasal cavity is open to allow a flow therethrough, on exhaling through the nasal airway, a pressure is developed in the one nasal cavity to which the delivery device is fitted and an exhalation air flow is developed through the other nasal cavity, as illustrated in FIG. 9(b). As illustrated in FIG. 9(b), the pressure which is developed in the one nasal cavity acts to expand the nasal valve therein, thereby facilitating the delivery of substance to posterior regions of the nasal airway.

On generation of a predetermined flow at the nosepiece 125, the actuation unit 129 is configured such as to be manually actuatable. In this embodiment the actuation unit 129 provides an indication to the user, typically as one or more of an audible, visual or tactile indication, when the predetermined flow rate is generated at the nosepiece 125.

Figure 9C:
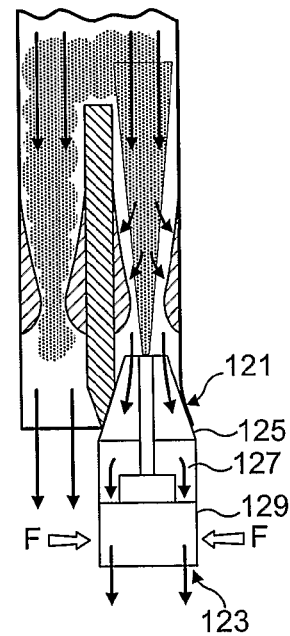

The user then actuates actuate the substance supply unit 127 to deliver substance through the nosepiece 125 and into the one nasal cavity, as illustrated in FIG. 9(c).

In one embodiment the substance supply unit 127 is configured to deliver substance with sufficient force as to be directed to a posterior region of the one nasal cavity, and be entrained by the exhalation air flow through the other nasal cavity. In this way, substance is entrained around the nasal septum, providing for improved delivery to the posterior region of the nasal airway.

In an alternative embodiment the substance supply unit 127 could be configured to deliver substance into the nosepiece 125, which substance becomes resident in the one nasal cavity and is drawn, in the manner of the Venturi effect, into the exhalation air flow through the other nasal cavity. In this way, substance is delivered around the nasal septum, providing for improved delivery to the posterior region of the nasal airway.

In one embodiment, and where required, the delivery device can be utilized to deliver substance to the respective nasal cavities of the subject by repeating the delivery operation.

Figure 10:
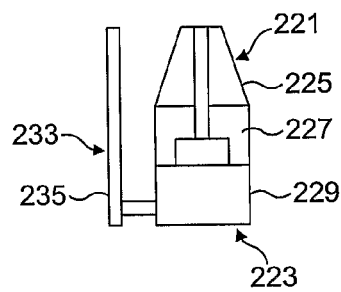

FIGS. 10 to 12 illustrate a nasal delivery device in accordance with a fourth embodiment of the present invention.

The delivery device comprises a nosepiece unit 221 for fitting to one nostril of a subject, and a delivery unit 223 for delivering a substance through the nosepiece unit 221 into the nasal cavity in response to exhalation or at least attempted exhalation by the subject through the nasal airway.

The nosepiece unit 221 includes a nosepiece 225 through which substance is delivered into the nasal cavity of the subject.

In this embodiment the nosepiece 225 comprises a tubular, frusto-conical element which is configured such as to be inserted into one nostril, and in a preferred embodiment provide a fluid-tight seal with the one nostril.

In an alternative embodiment the nosepiece 225 could comprise an annular element which is configured such as to engage the nares of the one nostril, and in a preferred embodiment provide a fluid-tight seal with the one nostril.

The delivery unit 223 includes a substance supply unit 227 for delivering a dose of a substance, in this embodiment a metered dose of a substance, and an actuation unit 229, in this embodiment a breath-actuation unit, which is in fluid communication with the nosepiece 225 and operative to actuate the substance supply unit 227 in response to exhalation or at least attempted exhalation by the subject through the nasal airway.

In this embodiment the substance supply unit 227 is configured to deliver substance with sufficient force as to be directed to a posterior region of the one nasal cavity.

In this embodiment the substance supply unit 227 comprises a liquid supply unit for delivering a liquid substance through the nosepiece 225.

In another embodiment the substance supply unit 227 could comprise powder supply unit for delivering a powdered substance through the nosepiece 225.

In this embodiment the substance supply unit 227 comprises an aerosol generator for delivering an aerosol of the substance through the nosepiece 225.

In an alternative embodiment the substance supply unit 227 comprises a jet generator for delivering a jet of the substance through the nosepiece 225.

In this embodiment the substance comprises a medicament, but the substance could be any kind of other substance, such as a vaccine.

In this embodiment the substance supply unit 227 comprises a pump unit, here a mechanical pump unit.

In an alternative embodiment the substance supply unit 227 could comprise an electrically-operated pump unit.

In another embodiment the substance supply unit 227 could comprise a nebulizer for delivering an aerosol, either as a liquid or powder aerosol, to the nosepiece 225.

The actuation unit 229 includes a release mechanism 233 which is manually operable to unlock the actuation unit 229, such as to render the actuation unit 229 operative in response to exhalation or at least attempted exhalation through the nasal airway.

Figure 11A:
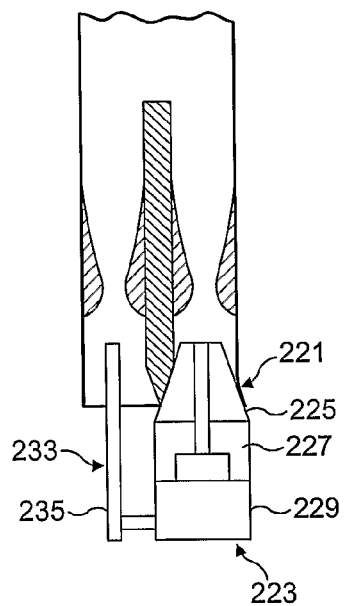
Figure 11B:
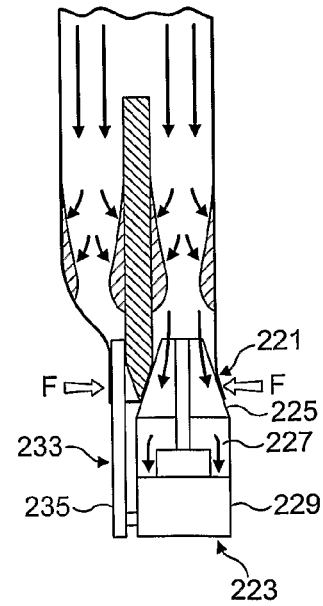
Figure 12A:
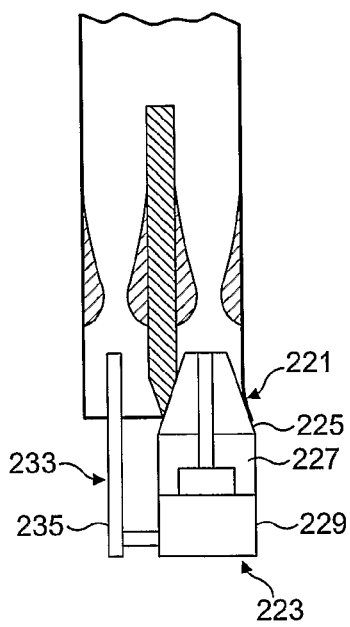
Figure 12B:
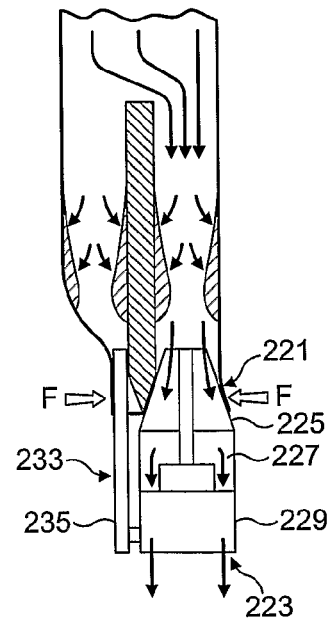

In this embodiment the release mechanism 233 comprises a movable member 235, which is manually operable between a first, locking state, as illustrated, for example, in FIGS. 11(a) and 12(a), in which the actuation unit 229 is locked to prevent operation in response to exhalation or at least attempted exhalation through the nasal airway, and a second, unlocked state, as illustrated, for example, in FIG. 11(b) or 12(b), in which the actuation unit 229 is unlocked to allow for operation in response to exhalation or attempted exhalation through the nasal airway.

In this embodiment the actuation unit 229 includes a pressure sensor for sensing the pressure at the nosepiece 225 and actuating the substance supply unit 227 in response to generation of a predetermined pressure.

In another embodiment the actuation unit 229 could include a flow sensor for sensing a flow through the nosepiece 225 and actuating the substance supply unit 227 in response to detection of a predetermined flow.

Figure 11C:
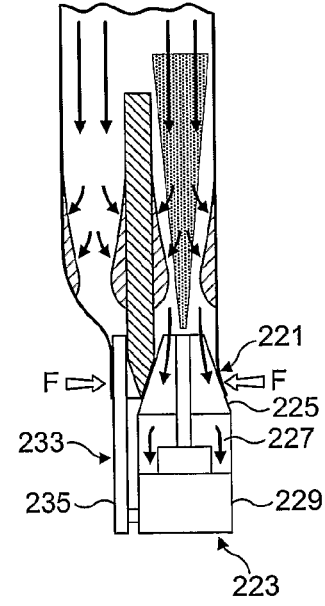

One mode of operation of the above-described delivery device will now be described hereinbelow with reference to FIGS. 11(a) to (c) of the accompanying drawings.

The subject first primes the delivery unit 221, in this embodiment by loading a biasing element, and then fits the nosepiece 225 to one nostril such that the movable member 235 of the release mechanism 233 extends at least to, and in this embodiment into the other nasal cavity, as illustrated in FIG. 11(a).

The subject then acts to close the other nasal cavity, in this embodiment by pinching the outer nares of the nostrils, and the applied force F acts to move the movable member 235 of the release mechanism 233 from the locked configuration to the unlocked configuration, as illustrated in FIG. 11(b), in which configuration the actuation unit 229 is in the operative state.

The subject then exhales through his or her nasal airway, as illustrated in FIG. 11(b).

In this embodiment, where the one nasal cavity is closed, on exhaling through the nasal airway or at least attempting to exhale through the nasal airway, a pressure is developed in both nasal cavities. As illustrated in FIG. 11(b), the pressure which is developed in the one nasal cavity acts to expand the nasal valve therein, thereby facilitating the subsequent delivery of substance to posterior regions of the nasal airway. On generation of a predetermined pressure at the nosepiece 225, the actuation unit 229 acts to actuate the substance supply unit 227 to deliver substance through the nosepiece 225 and into the one nasal cavity, as illustrated in FIG. 11(c). Owing to the positive pressure which is developed in the nasal airway by attempted exhalation, the delivered substance remains within the nasal airway, with any residual substance being flushed from the nasal airway on release of the applied force F in removal of the delivery device.

In one embodiment, and where required, the delivery device can be utilized to deliver substance to the respective nasal cavities of the subject by repeating the delivery operation.

Figure 12C:
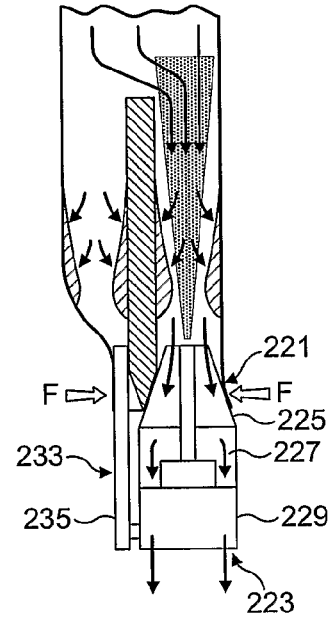

Another mode of operation of the above-described delivery device will now be described hereinbelow with reference to FIGS. 12(a) to (c) of the accompanying drawings.

The subject first primes the delivery unit 221, in this embodiment by loading a biasing element, and then fits the nosepiece 225 to one nostril such that the movable member 235 of the release mechanism 233 extends at least to, and in this embodiment into the other nasal cavity, as illustrated in FIG. 12(a).

The subject then acts to close the other nasal cavity, in this embodiment by pinching the outer nares of the nostrils, and the applied force F acts to move the movable member 235 of the release mechanism 233 from the locked configuration to the unlocked configuration, as illustrated in FIG. 12(b), in which configuration the actuation unit 229 is in the operative state.

The subject then exhales through his or her nasal airway, as illustrated in FIG. 12(b).

In this embodiment, where the one nasal cavity is partially open to allow a flow therethrough, which provides an indication to the subject of the establishment of proper exhalation, on exhaling through the nasal airway, a small flow is developed through the one nasal cavity to which the delivery device is fitted and a pressure is developed in the nasal airway. As illustrated in FIG. 12(b), the pressure which is developed in the one nasal cavity acts to expand the nasal valve therein, thereby facilitating the subsequent delivery of substance to posterior regions of the nasal airway. On generation of a predetermined flow rate through the nosepiece 225, the actuation unit 229 acts to actuate the substance supply unit 227 to deliver substance through the nosepiece 225 and into the one nasal cavity, as illustrated in FIG. 12(c). Owing to the positive pressure which is developed in the nasal airway by attempted exhalation, the delivered substance remains substantially within the nasal airway, with any residual substance being flushed from the nasal airway on release of the applied force F in removal of the delivery device.

In one embodiment, and where required, the delivery device can be utilized to deliver substance to the respective nasal cavities of the subject by repeating the delivery operation.

Figure 13:
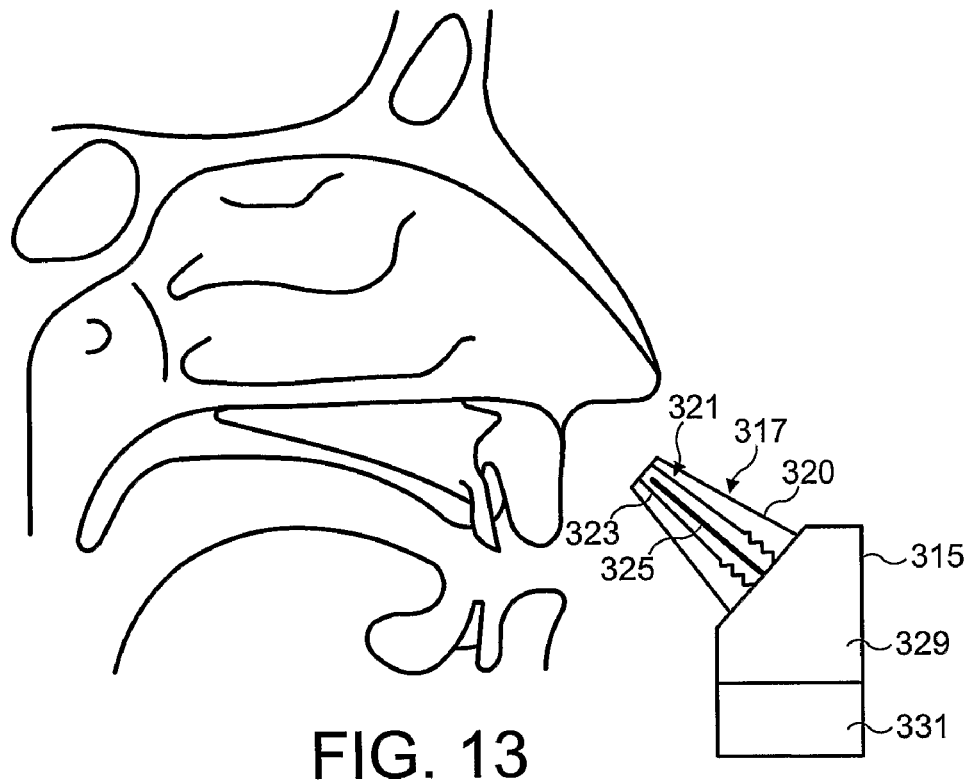
Figure 14:
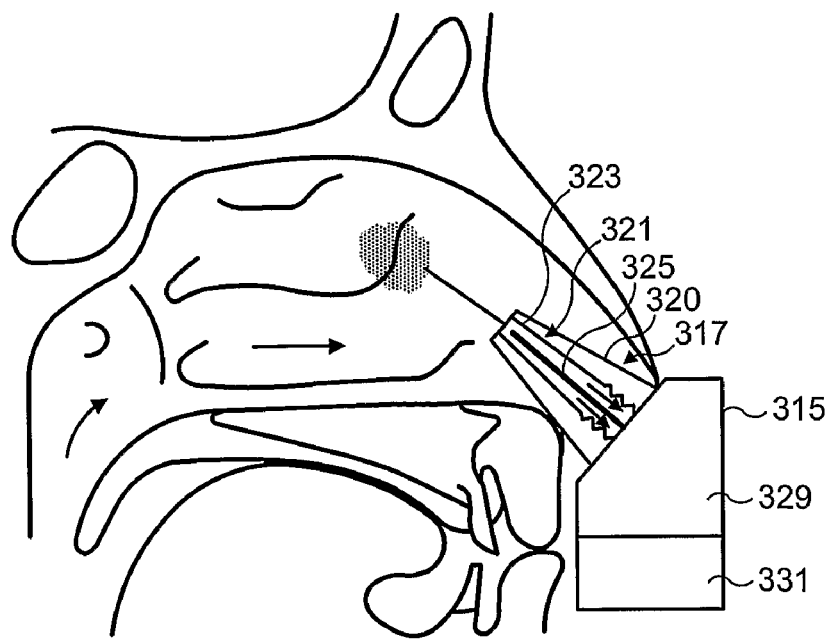
FIG. 14 illustrates the delivery device of FIG. 13 where operative to deliver a dose of substance into the nasal airway of the subject.
Figure 15:
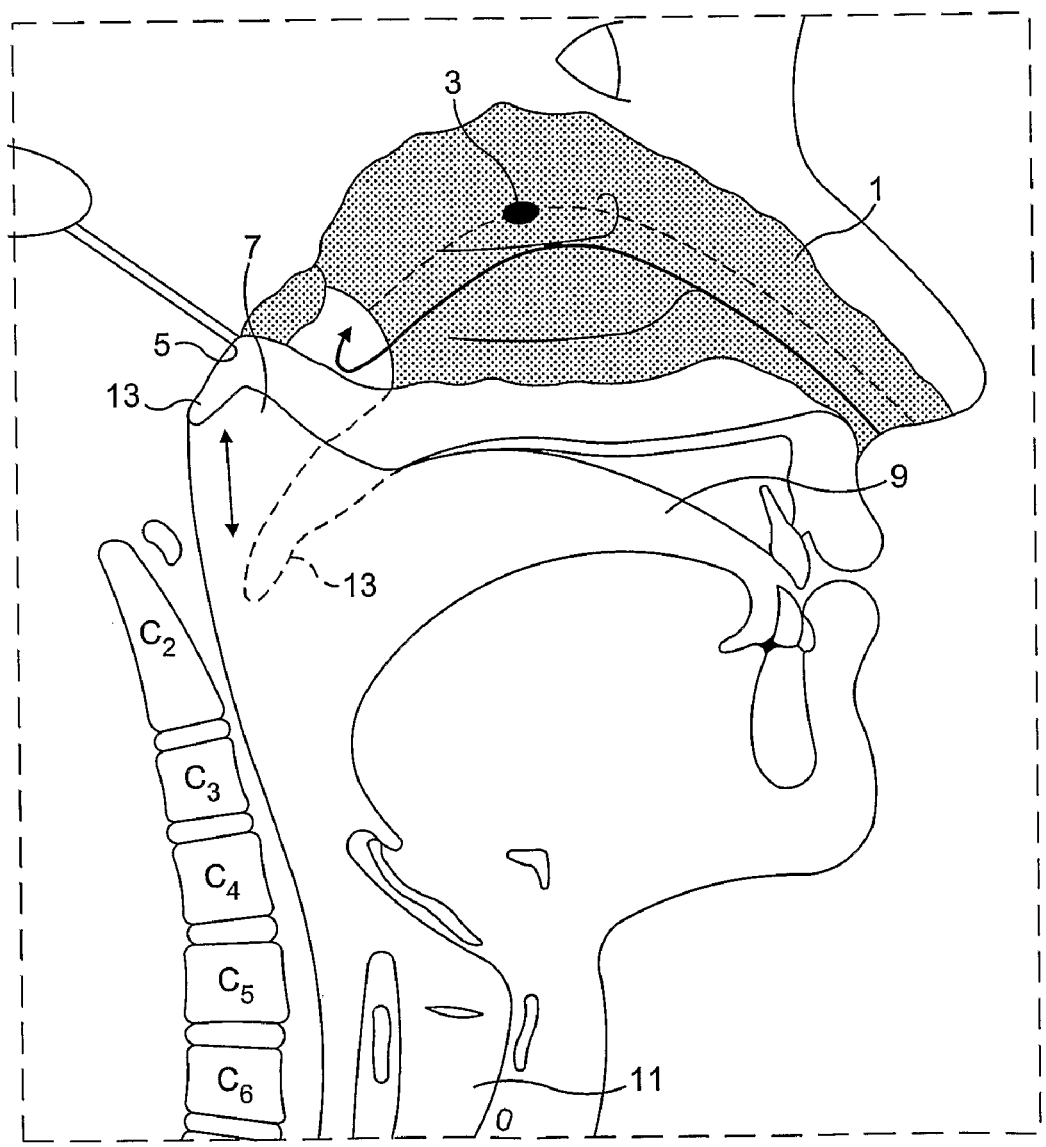
FIG. 15 schematically illustrates the anatomy of the upper respiratory tract of a human subject.

FIGS. 13 and 14 illustrate a nasal delivery device in accordance with a fifth embodiment of the present invention.

The delivery device comprises a housing 315, and a nosepiece unit 317 for fitting in a nasal cavity of a subject and into which the subject nasally exhales to actuate the delivery device.

The nosepiece unit 317 comprises a nosepiece 320, in this embodiment a frusto-conical element, for guiding the nosepiece unit 317 into a nasal cavity of the subject and being configured both to provide a fluid-tight seal with the nares of the nostril and at least obstruct, in this embodiment close, the nasal passage at a position therealong, in this embodiment at a position corresponding substantially to the nasal valve, thereby obstructing the anterior one-third of the nasal cavity and leaving open the posterior two-thirds of the nasal cavity, as illustrated in FIG. 14.

In this embodiment the nosepiece 320 is further configured such as mechanically to open the nasal valve, thereby facilitating access to the posterior two-thirds of the nasal cavity.

The nosepiece unit 317 further comprises an outlet unit 321 for delivering substance into the nasal cavity of the subject.

In this embodiment the outlet unit 321 comprises a communication channel 323 which is in fluid communication with the nasal cavity of the subject, such as to enable nasal exhalation to be detected through the generation of an increased pressure thereat, and a nozzle 325 for delivering a metered dose of substance into the nasal cavity of the subject.

In this embodiment the nozzle 325 is configured to deliver a jet, as a column of substance, either of liquid or powder.

In an alternative embodiment the nozzle 325 could be configured to deliver an aerosol spray of substance, either of liquid or powder, as in the above-described embodiments.

The delivery device further comprises a substance supply unit 329 for delivering metered doses of the substance, which is fluidly connected to the nozzle 325 to deliver the substance from the nosepiece unit 317, in this embodiment as a jet.

In this embodiment the substance supply unit 329 comprises a mechanical delivery pump.

In this embodiment the substance supply unit 329 is a multi-dose unit for delivering a plurality of metered doses of the substance. In another embodiment the substance supply unit 329 could be a single-dose unit for delivering a single metered dose of the substance.

The substance supply unit 329 is pre-primeable, in this embodiment by loading a resilient element, and includes a breath-actuated release mechanism 331 which, when triggered by nasal exhalation, releases the resilient element and actuates the substance supply unit 329 to deliver a metered dose of the substance through the nozzle 325.

In this embodiment the release mechanism 331 is configured to cause actuation of the substance supply unit 329 on generation of a predetermined pressure at the communication channel 323, which is developed in response to nasal exhalation.

The generation of a raised pressure in the nasal cavity acts to expand the posterior region of the nasal cavity, and also acts to force substance into ducts and channels leading to the sinuses, which can, for example, be blocked by mucosal inflammation and polyps.

Operation of the delivery device will now be described hereinbelow with reference to FIG. 14 of the accompanying drawings.

The nosepiece unit 317 is first inserted into one of the nasal cavities of a subject until the nosepiece 320 abuts the nares of the nostril, such as to establish a fluid-tight seal therewith, at which point the distal end of the outlet unit 321 extends about 2 cm into the nasal cavity of the subject such as to engage and expand the nasal valve.

The subject then begins to exhale nasally, which exhalation acts to generate an increased pressure in the one nasal cavity. In this embodiment the mouth of the subject can be closed, or the mouth can remain open and the tongue be positioned such as to prevent oral exhalation, as illustrated in FIG. 14.

In this embodiment, when the pressure developed at the communication channel 323 reaches a predetermined value, the release mechanism 331 is triggered to actuate the substance supply unit 329 to deliver a metered dose of the substance to the nozzle 325 and into the nasal cavity of the subject, here as a jet.

In this embodiment the delivery device is configured such that at least 50% of the dose as initially deposited in the nasal cavity is deposited in a region of the nasal cavity which is posterior of the nasal valve, and at least 30% of the dose as initially deposited in the nasal cavity is deposited in an upper posterior region of the nasal cavity which is posterior of the nasal valve and above the inferior meatus.

In preferred embodiments the delivery device is configured such that at least 55%, more preferably at least 60%, still more preferably at least 65% and yet more preferably 70% of the dose as initially deposited in the nasal cavity is deposited in the region posterior of the nasal valve.

In preferred embodiments the delivery device is configured such that at least 35%, more preferably at least 40%, still more preferably at least 45% and yet more preferably 50% of the dose as initially deposited in the nasal cavity is deposited in the upper posterior region of the nasal cavity.

In this embodiment, where the delivery device is a multi-dose device, the device is ready for further use following priming of the pump unit 329.

In one alternative embodiment the nozzle 325 could be configured to deliver a plurality of liquid jets.

In one embodiment the contralateral nostril can be partially or wholly obstructed, such as to promote the generation of a raised pressure in the nasal cavity into which substance is to be delivered. In one embodiment the contralateral nostril can be obstructed by applying a pressure to the lateral nare of the contralateral nostril. In another embodiment the nosepiece unit 317 can include a second nosepiece 320 which is configured to be fitted in the other nostril of the subject such as to obstruct the same.

Finally, it will be understood that the present invention has been described in its preferred embodiments and can be modified in many different ways without departing from the scope of the invention as defined by the appended claims.

For example, in one modification, the delivery device of the first-described embodiment could be modified to include first and second nosepiece units 21 which are fluidly connected to the delivery unit 23. In one embodiment the delivery device could include first and second delivery units 23 which provide for the delivery of different substances to the nasal airway.

In another modification, the delivery devices of the second and fourth embodiments could be modified such as to be manually actuatable in the manner of the third-described embodiment.

The invention claimed is:

1. A delivery device for delivering substance to a nasal airway of a subject, the delivery device comprising:
    at least one nosepiece unit for insertion into one nasal cavity of a subject and comprising a nosepiece for fitting to the respective nostril of the subject; and
    at least one delivery unit which is operative to deliver a substance through the at least one nosepiece unit into the one nasal cavity of the subject, wherein the at least one delivery unit includes a substance supply unit for delivering a substance and an actuation unit which is operable to actuate the substance supply unit in response to nasal exhalation or at least attempted nasal exhalation by the subject.

2. The delivery device of claim 1, wherein the substance supply unit is configured to deliver an aerosol spray.

3. The delivery device of claim 2, wherein the aerosol spray is a liquid aerosol.

4. The delivery device of claim 2, wherein the aerosol spray is a powder aerosol.

5. The delivery device of claim 1, wherein the substance supply unit is configured to deliver a liquid jet.

6. The delivery device of claim 1, wherein the substance supply unit is configured to deliver a powder jet.

7. The delivery device of claim 1, wherein the nosepiece is configured to provide a fluid-tight seal with the one nostril of the subject.

8. The delivery device of claim 1, wherein the actuation unit includes a pressure sensor for sensing the pressure at the nosepiece and actuating the substance supply unit in response to a predeterminable pressure.

9. The delivery device of claim 1, wherein the actuation unit includes a flow sensor for sensing the flow rate at the nosepiece and actuating the substance supply unit in response to a predeterminable flow rate.

10. The delivery device of claim 1, wherein the actuation unit includes a pressure sensor for sensing the pressure at the nosepiece and is operative such as to allow for manual actuation of the substance supply unit only in response to the pressure sensor sensing a predeterminable pressure.

11. The delivery device of claim 1, wherein the actuation unit includes a flow sensor for sensing the flow rate at the nosepiece and is operative such as to allow for manual actuation of the substance supply unit only in response to the flow sensor sensing a predeterminable flow rate.

12. The delivery device of claim 1, wherein the substance supply unit is configured to deliver substance with sufficient force as to be directed to a posterior region of the one nasal cavity, and be entrained by an exhalation air flow through the other nasal cavity.

13. The delivery device of claim 1, wherein the substance supply unit is configured to deliver substance into the one nasal cavity, and be drawn from the one nasal cavity by an exhalation air flow through the other nasal cavity.

14. The delivery device of claim 1, comprising: first and second nosepiece units for fitting to the respective nostrils of the subject, wherein the substance supply unit is in fluid communication with the first nosepiece unit such that substance is in use delivered into the one nasal cavity and the actuation unit is in fluid communication with the second, outlet nosepiece unit.

15. The delivery device of claim 14, wherein the delivery unit includes a filter unit which is in fluid communication with the second, outlet nosepiece unit.

16. The delivery device of claim 1, wherein the actuation unit includes a release mechanism which is manually operable to unlock the actuation unit, such as to render the actuation unit operative in response to nasal exhalation or at least attempted nasal exhalation by the subject.

17. The delivery device of claim 16, wherein the release mechanism comprises a movable member which is manually operable between a first, locking configuration in which the actuation unit is locked to prevent operation in response to nasal exhalation or at least attempted nasal exhalation by the subject, and a second, unlocked configuration in which the actuation unit is unlocked to allow for operation in response to nasal exhalation or at least attempted exhalation by the subject.

18. The delivery device of claim 17, wherein the movable member in use extends into the other nasal cavity, such that the other nostril of the subject is closed when the movable member is in the unlocked configuration.

19. A method of delivering substance to a nasal airway of a subject, the method comprising the steps of:
    providing a delivery device comprising a nosepiece unit including a nosepiece for fitting to one nasal cavity of a subject, and a delivery unit including a substance supply unit for delivering substance and an actuation unit which is operable to actuate the substance supply unit in response to nasal exhalation or at least attempted nasal exhalation by the subject;
    fitting the nosepiece unit to one nasal cavity of a subject; the subject exhaling nasally or at least attempting to exhale nasally; and actuating the substance supply unit to deliver substance to the one nasal cavity in response to nasal exhalation or at least attempted nasal exhalation.

20. The method of claim 19, wherein the substance supply unit is delivered as an aerosol spray.

21. The method of claim 20, wherein the aerosol spray is a liquid aerosol.

22. The method of claim 20, wherein the aerosol spray is a powder aerosol.

23. The method of claim 19, wherein the substance is delivered as a liquid jet.

24. The method of claim 19, wherein the substance is delivered as a powder jet.

25. The method of claim 19, wherein the actuation unit includes a pressure sensor for sensing the pressure at the nosepiece and is operative to actuate the substance supply unit in response to the pressure sensor sensing a predeterminable pressure.

26. The method of claim 19, wherein the actuation unit includes a flow sensor for sensing the flow rate at the nosepiece and is operative to actuate the substance supply unit in response to the flow sensor sensing a predeterminable flow rate.

27. The method of claim 19, wherein the actuation unit includes a pressure sensor for sensing the pressure at the nosepiece and is configured to allow for manual actuation of the substance supply unit only in response to the pressure sensor sensing a predeterminable pressure, and the actuating step comprises the step of: manually actuating the substance supply unit to deliver substance to the one nasal cavity.

28. The method of claim 19, wherein the actuation unit includes a flow sensor for sensing the flow rate at the nosepiece and is configured to allow for manual actuation of the substance supply unit only in response to the flow sensor sensing a predeterminable flow rate, and the actuating step comprises the step of: manually actuating the substance supply unit to deliver substance to the one nasal cavity.

29. The method of claim 19, wherein the nosepiece unit is configured to close the one nostril of the subject.

30. The method of claim 19, wherein the nosepiece unit is configured to allow an air flow from the one nostril of the subject on nasal exhalation by the subject.

31. The method of claim 19, wherein the substance supply unit is configured to deliver substance with sufficient force as to be directed to a posterior region of the one nasal cavity, and an exhalation air flow is generated through the other nasal cavity which acts to entrain the delivered substance.

32. The method of claim 19, wherein the substance supply unit is configured to deliver substance into the one nasal cavity, and an exhalation air flow is generated through the other nasal cavity which acts to draw the delivered substance from the one nasal cavity.

33. The method of claim 19, wherein the delivery device comprises first and second nosepiece units for fitting to the respective nostrils of the subject, wherein the substance supply unit is in fluid communication with the first nosepiece unit such that substance is delivered into the one nasal cavity and the actuation unit is in fluid communication with the second, outlet nosepiece unit.

34. The method of claim 33, wherein the delivery unit includes a filter unit which is in fluid communication with the second, outlet nosepiece unit and acts to trap any substance as delivered from the other nostril of the subject.

35. The method of claim 19, wherein the actuation unit includes a release mechanism which is manually operable to unlock the actuation unit, such as to render the actuation unit operative in response to nasal exhalation or at least attempted nasal exhalation by the subject.

36. The method of claim 35, wherein the release mechanism comprises a movable member which is manually operable between a first, locking configuration in which the actuation unit is locked to prevent operation in response to nasal exhalation or at least attempted nasal exhalation by the subject, and a second, unlocked configuration in which the actuation unit is unlocked to allow for operation in response to nasal exhalation or at least attempted nasal exhalation by the subject.

37. The method of claim 36, wherein the movable member extends into the other nasal cavity, such that movement of the movable member to the unlocked configuration requires closure of the other nostril of the subject.

* * * * *